United States Patent
Fishel

(10) Patent No.: US 12,408,924 B2
(45) Date of Patent: Sep. 9, 2025

(54) MECHANISM AND DEVICE FOR LEFT ATRIAL APPENDAGE OCCLUSION WITH ELECTRICAL ISOLATION

(71) Applicant: Robert S. Fishel, Palm Beach, FL (US)

(72) Inventor: Robert S. Fishel, Palm Beach, FL (US)

( * ) Notice: Subject to any disclaimer, the term of this patent is extended or adjusted under 35 U.S.C. 154(b) by 1204 days.

(21) Appl. No.: 17/063,237

(22) Filed: Oct. 5, 2020

(65) Prior Publication Data
US 2021/0085388 A1   Mar. 25, 2021

Related U.S. Application Data

(63) Continuation-in-part of application No. 15/977,202, filed on May 11, 2018, now Pat. No. 11,357,512.
(Continued)

(51) Int. Cl.
*A61B 17/12* (2006.01)
*A61B 18/14* (2006.01)
(Continued)

(52) U.S. Cl.
CPC .. *A61B 17/12122* (2013.01); *A61B 17/12145* (2013.01); *A61B 18/1492* (2013.01);
(Continued)

(58) Field of Classification Search
CPC ........ A61B 17/12122; A61B 17/12031; A61B 17/12131; A61B 2017/12095;
(Continued)

(56) References Cited

U.S. PATENT DOCUMENTS

| 4,364,392 A | 12/1982 | Strother et al. |
| 7,620,476 B2 | 11/2009 | Morse et al. |

(Continued)

FOREIGN PATENT DOCUMENTS

| CN | 106208276 A | 12/2016 |
| EP | 2366964 A1 | 9/2011 |

(Continued)

OTHER PUBLICATIONS

International Preliminary Report on Patentability for International Application No. PCT/US2018/015221, mailed Apr. 12, 2019, eight (8) pages.
(Continued)

*Primary Examiner* — Joanne M Rodden
*Assistant Examiner* — Dana Stumpfoll
(74) *Attorney, Agent, or Firm* — Brown Rudnick LLP; Matthew P. York

(57) ABSTRACT

Left atrial appendage (LAA) occlusion device including a membrane, a plurality of fixation splines, at least two electrical conductors and an interconnect, the interconnect positioned in the membrane for coupling the fixation splines and the electrical conductors, the fixation splines for affixing the LAA occlusion device to an ostium of the LAA and the electrical conductors for applying high voltage electricity to the ostium of the LAA, wherein the membrane physically occludes the LAA and the electrical conductors are used to electroporate the ostium of the LAA via the high voltage electricity, thereby electrically isolating the LAA.

23 Claims, 9 Drawing Sheets

Related U.S. Application Data

(60) Provisional application No. 62/505,155, filed on May 12, 2017.

(51) Int. Cl.
| | |
|---|---|
| *A61M 5/00* | (2006.01) |
| *A61B 17/00* | (2006.01) |
| *A61B 18/00* | (2006.01) |
| *A61B 18/16* | (2006.01) |
| *A61M 5/14* | (2006.01) |
| *A61N 1/20* | (2006.01) |
| *A61N 1/32* | (2006.01) |

(52) U.S. Cl.
CPC ... *A61M 5/007* (2013.01); *A61B 2017/00893* (2013.01); *A61B 2017/00951* (2013.01); *A61B 2017/1205* (2013.01); *A61B 17/1215* (2013.01); *A61B 2018/00077* (2013.01); *A61B 2018/00375* (2013.01); *A61B 2018/00613* (2013.01); *A61B 18/16* (2013.01); *A61M 5/14* (2013.01); *A61N 1/205* (2013.01); *A61N 1/32* (2013.01)

(58) Field of Classification Search
CPC .... A61B 17/12036; A61B 2017/00243; A61B 2017/12054; A61B 17/12172; A61B 2017/00929; A61B 2018/00613; A61M 25/0075; A61M 25/0662; A61M 2025/0076; A61M 2210/125; A61N 1/32
See application file for complete search history.

(56) References Cited

U.S. PATENT DOCUMENTS

| | | | |
|---|---|---|---|
| 8,500,918 | B1 | 8/2013 | Meller et al. |
| 9,080,791 | B1 | 7/2015 | Meller et al. |
| 9,130,502 | B1 | 9/2015 | Aly et al. |
| 9,455,665 | B1 | 9/2016 | Meller et al. |
| 9,931,009 | B2 | 4/2018 | Miyake et al. |
| 10,391,637 | B2 | 8/2019 | Miyake et al. |
| 2003/0120337 | A1 | 6/2003 | Van Tassel et al. |
| 2003/0220667 | A1 | 11/2003 | van der Burg et al. |
| 2005/0288706 | A1* | 12/2005 | Widomski ....... A61B 17/12136 606/213 |
| 2006/0074410 | A1* | 4/2006 | Malecki ............ A61B 18/1492 606/32 |
| 2007/0142964 | A1 | 6/2007 | Abramson |
| 2008/0011288 | A1 | 1/2008 | Olsson |
| 2008/0140255 | A1 | 6/2008 | Ziegler et al. |
| 2009/0049640 | A1 | 2/2009 | Lee et al. |
| 2012/0040179 | A1 | 2/2012 | Dave |
| 2013/0018413 | A1* | 1/2013 | Oral ................ A61B 17/12186 606/213 |
| 2013/0138138 | A1 | 5/2013 | Clark et al. |
| 2013/0234645 | A1 | 9/2013 | Goei et al. |
| 2014/0277074 | A1 | 9/2014 | Kaplan et al. |
| 2014/0350592 | A1 | 11/2014 | Kreidler et al. |
| 2014/0379020 | A1 | 12/2014 | Campbell et al. |
| 2015/0133989 | A1 | 5/2015 | Lubock et al. |
| 2015/0229265 | A1 | 8/2015 | Morita et al. |
| 2015/0236640 | A1 | 8/2015 | Miyake et al. |
| 2015/0272413 | A1 | 10/2015 | Miyake et al. |
| 2016/0074043 | A1 | 3/2016 | Friedman et al. |
| 2016/0332748 | A1 | 11/2016 | Wang |
| 2016/0374754 | A1* | 12/2016 | Asirvatham ........... A61B 18/02 606/41 |
| 2017/0095257 | A1 | 4/2017 | Miller et al. |
| 2017/0100112 | A1 | 4/2017 | van der Burg et al. |
| 2017/0164797 | A1 | 6/2017 | Abramson et al. |
| 2017/0281193 | A1 | 10/2017 | Asirvatham et al. |
| 2018/0054156 | A1 | 2/2018 | Lokey |
| 2018/0116678 | A1* | 5/2018 | Melanson ........ A61B 17/12181 |
| 2018/0161039 | A1* | 6/2018 | Harks .............. A61B 17/12122 |
| 2018/0333562 | A1* | 11/2018 | Pagoria .................... A61F 2/90 |
| 2018/0338767 | A1 | 11/2018 | Dasnurkar et al. |
| 2020/0008870 | A1* | 1/2020 | Gruba .................. A61B 18/082 |

FOREIGN PATENT DOCUMENTS

| | | | |
|---|---|---|---|
| EP | 3636171 | A1 | 4/2020 |
| FR | 3022360 | A1 | 12/2015 |
| WO | 0130268 | A1 | 5/2001 |
| WO | 2010/003115 | A1 | 1/2010 |
| WO | 2014/196480 | A1 | 12/2014 |
| WO | 2015/152431 | A1 | 10/2015 |
| WO | 2018/228383 | A1 | 12/2018 |
| WO | 2019/136218 | A1 | 7/2019 |
| WO | 2019/166017 | A1 | 9/2019 |

OTHER PUBLICATIONS

International Search Report and Written Opinion of the International Searching Authority mailed Apr. 5, 2018, for International Application No. PCT/US2018/015221 (17 pages).
Notice of Allowance issued in U.S. Appl. No. 15/977,202, date of mailing: Mar. 25, 2022, 13 pages.
Non-Final Office Action issued in U.S. Appl. No. 15/977,202, date of mailing: Sep. 28, 2021, 15 pages.
International Search Report issued in International Application No. PCT/US2021/053144, date of mailing: Dec. 10, 2021, 10 pages.
Examination Report issued in GB Application No. GB2305053.7, date of mailing: Oct. 1, 2024, 4 pages.
Extended European Search Report issued is European Application No. 21878268.8, date of mailing: Sep. 18, 2024, 8 pages.

* cited by examiner

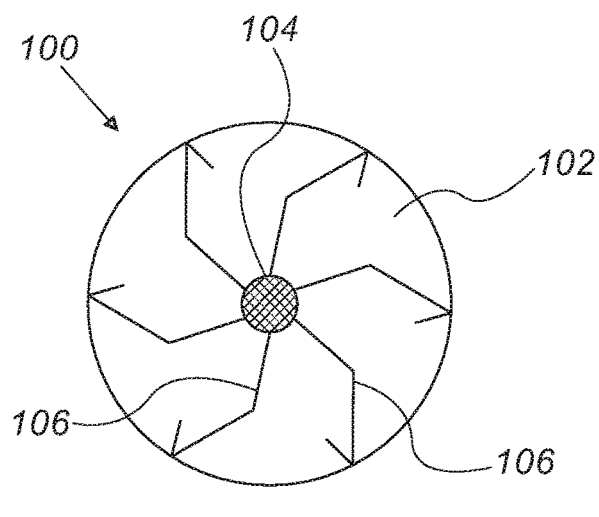
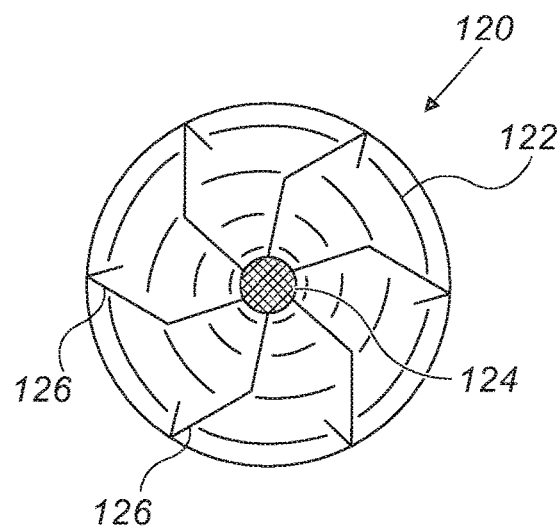
FIG. 2A  FIG. 2B
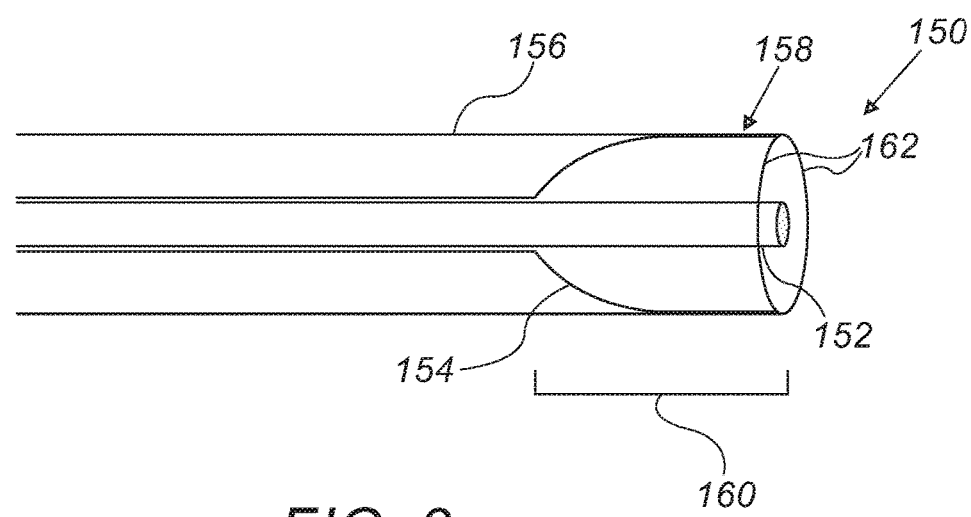
FIG. 3

MECHANISM AND DEVICE FOR LEFT ATRIAL APPENDAGE OCCLUSION WITH ELECTRICAL ISOLATION

FIELD OF THE DISCLOSED TECHNIQUE

The disclosed technique relates to left atrial appendage occlusion, in general, and to methods and system for occluding as well as electrically isolating the left atrial appendage, in particular.

BACKGROUND OF THE DISCLOSED TECHNIQUE

The left atrial appendage (herein abbreviated LAA) is a contracting sac of tissue located in the upper anterior section of the left atrium of the heart. In a normal heart, the LAA plays an important role in atrial capacitance and is a contractile structure. In certain heart diseases and arrhythmias, most notably atrial fibrillation (herein abbreviated AF), the LAA can become a source for blood pooling and subsequent thrombus and embolus (i.e., blood clot) formation and embolization. AF is characterized by a rapid and irregular beating of the atria, which can lead to blood to move back and forth between the ventricles and the atria, leading to the formation of blood clots and thrombi in the LAA. Such blood clots can eventually leave the LAA and enter the blood stream, causing blockages in the passages or organs of the body (medically referred to as an embolization). Thrombus formation in the LAA accounts for the majority of cardioembolic events, such as strokes, in patients with AF. Reference is now made to FIG. 1, which is a schematic illustration of a heart showing the formation of a blood clot, generally referenced 10, as is known in the art. FIG. 1 shows a heart with a right atrium (herein abbreviated RA) 12, a right ventricle (herein abbreviated RV) 14, a left atrium (herein abbreviated LA) 16 and a left ventricle (herein abbreviated LV) 18. An LAA 20 is shown protruding from LA 16. A mitral valve 26 controls the blood flow between LA 16 and LV 18. Blood in the heart normally flows from RA 12 to RV 14 and from LA 16 to LV 18. In a patient suffering from AF, due to the irregularities of when mitral valve 26 opens and closes, blood from LV 18 may travel back to LA 16, as shown by an arrow 22. This blood may then travel to LAA 20 and form a thrombus 24, which can eventually pass through mitral valve 26 in LV 18 and then into the blood stream of the patient.

Known in the prior art are a series of devices which have been developed whose purpose is to occlude the LAA and thus prevent thrombus formation in the LAA and possible future embolization. Typically such devices have a semipermeable filter on their face and are deployed via catheter to the opening of the LAA where they are deployed. After device deployment, through the natural process of endothelialization, the filter becomes covered with endothelium thus sealing off the LAA and isolating this source of emboli. Other devices are known which clamp or physically close the opening of the LAA thus preventing the entry of blood and the possibility of thrombus formation. Examples are such devices are shown in US patent application publication numbers 2017/0100112, 2017/0095257, 2016/0074043, 2015/0133989, 2014/0379020, 2014/0277074 and 2013/0138138.

All prior art devices developed to date while being generally effective in mechanically isolating the LAA from the left atrium fail to electrically isolate this structure from the left atrium. Therefore arrhythmias such as AF originating in the LAA can still conduct into the remainder of the heart and can cause health issues. Studies have shown that in certain patients with AF, the LAA is the major driver of the arrhythmia and isolation or amputation of the LAA will control or help to control the underlying cardiac arrhythmia. For example, approximately one third of patients who undergo LAA amputation at the time of mitral valve repair are found to have spontaneous resolution of otherwise previously persistent AF on post-operative follow-up. Many patients who undergo LAA occlusion device placement are still symptomatic with the underlying arrhythmia, such as AF, and while the stroke risk is decreased after the LAA has been occluded, the patient nonetheless remains symptomatic of AF.

What is needed is therefore a method and system for occluding the LAA while also electrically isolating it such that emboli formation is prevented and AF originating from the LAA is eliminated.

SUMMARY OF THE DISCLOSED TECHNIQUE

The disclosed technique provides for a novel LAA occlusion device with electrical isolation and a novel method for occluding the LAA and isolating it electrically from the rest of the heart, which overcome the disadvantages of the prior art.

According to an aspect of the disclosed technique, there is thus provided a left atrial appendage (LAA) occlusion device including a membrane, a plurality of fixation splines, at least two electrical conductors and an interconnect. The interconnect is positioned in the membrane and is for coupling the fixation splines and the electrical conductors. The fixation splines are for affixing the LAA occlusion device to an ostium of the LAA and the electrical conductors are for applying high voltage electricity to the ostium of the LAA. The membrane physically occludes the LAA and the electrical conductors are used to electroporate the ostium of the LAA via the high voltage electricity, thereby electrically isolating the LAA.

According to another aspect of the disclosed technique, there is thus provided a left atrial appendage (LAA) occlusion device including a membrane, a plurality of conductive fixation splines and an interconnect. The interconnect is positioned in the membrane and is electrically coupled with the conductive fixation splines. The conductive fixation splines are for affixing the LAA occlusion device to an ostium of the LAA and for conducting electrical current. A positive conductor and a negative conductor can be coupled with the interconnect for providing high voltage electricity to the conductive fixation splines for electroporating the ostium of the LAA.

According to a further aspect of the disclosed technique, there is thus provided a method for deploying a left atrial appendage (LAA) occlusion system in a patient. The LAA occlusion system includes a membrane, an interconnect and at least two electrical conductors. The interconnect is positioned in the membrane. The method includes the procedures of inserting a guidewire into the patient for accessing a right atrium of a heart of the patient, puncturing a transseptal point in the heart for enabling access to the LAA and moving an injection tube loaded with the LAA occlusion system over the guidewire such that the LAA occlusion system is within the LAA. The method also includes the procedures of deploying the LAA occlusion system such that the membrane is affixed to tissue forming an ostium of the LAA and coupling an electrical wire to the interconnect via the injection tube. The method further includes the procedures of applying high voltage electricity to the electrical conductors, thereby electroporating the ostium of the LAA and removing the electrical wire, the injection tube and the guidewire.

BRIEF DESCRIPTION OF THE DRAWINGS

The disclosed technique will be understood and appreciated more fully from the following detailed description taken in conjunction with the drawings in which:

FIGS. 2A and 2B are schematic illustrations of a first and second embodiment of an LAA occlusion device, constructed and operative in accordance with an embodiment of the disclosed technique;

FIG. 3 is a schematic illustration of an isolation device and a delivery sheath, constructed and operative in accordance with another embodiment of the disclosed technique;

DETAILED DESCRIPTION OF THE EMBODIMENTS

Figure 1:
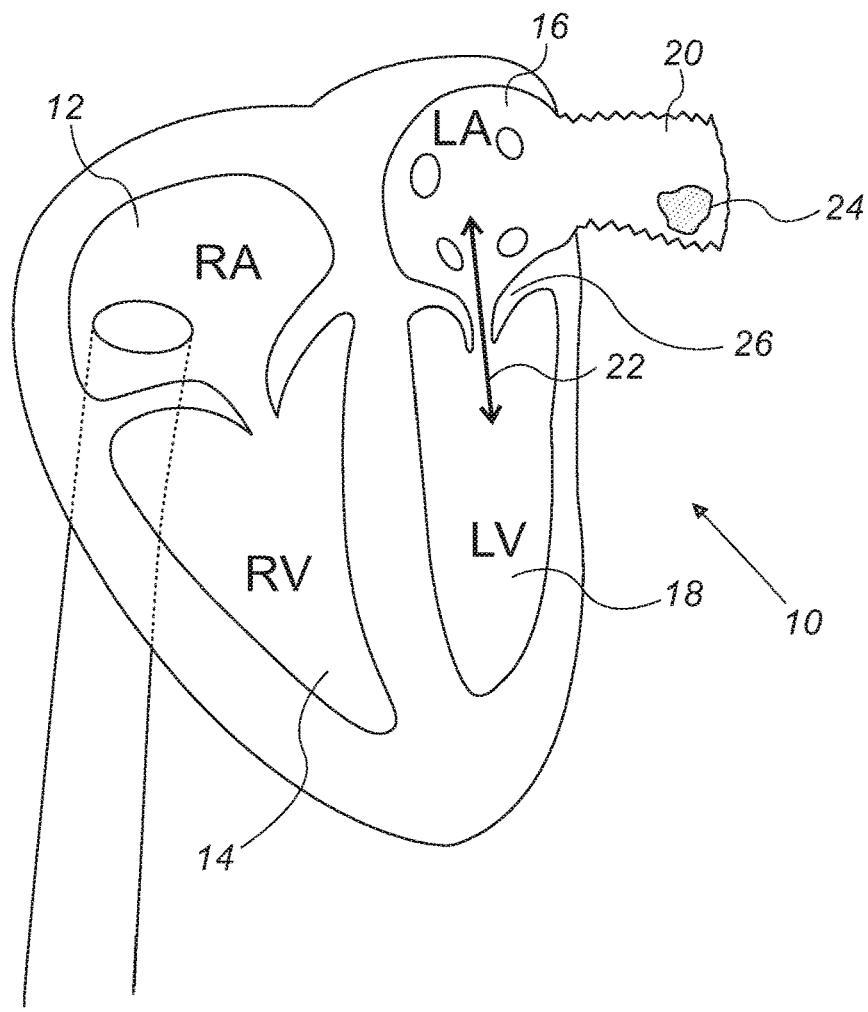
FIG. 1 is a schematic illustration of a heart showing the formation of a blood clot, as is known in the art.

The disclosed technique overcomes the disadvantages of the prior art by providing an occlusion device and system which is deployed at the ostium (i.e., opening) of the LAA. The occlusion device has either a semi-permeable or impermeable membrane for covering the ostium of the LAA and may have a plurality of fixation splines for holding the occlusion device in place. The occlusion device may also be held in place using staples and/or a glue. The occlusion device may further be held in place using an additional device such as a balloon catheter. Once deployed, the LAA is physically isolated from the LA. In one embodiment, the occlusion device also includes a hollow central deployment hub, embodied as a one-way valve, such as a diaphragm valve, for injecting a toxin or drug into the LAA. Following device deployment, a drug or toxin is infused via the deployment hub into the endoluminal appendage space of the LAA for killing the tissue therein and thus electrically isolating the LAA from the rest of the heart. The drug or toxin can be embodied as any biological inhibitor of cellular function, such as a viral vector, a drug, a medication and the like. In another embodiment, the occlusion device includes at least two electrical conductors for passing high voltage electricity as either direct current (herein abbreviated as DC) or alternating current (herein abbreviated AC) through the tissue at the rim of the ostium of the LAA thus killing the tissue therein via electroporation and electrically isolating the LAA from the rest of the heart. The electrical conductors may also pass electricity through the plurality of fixation splines. This embodiment may optionally include a deployment hub for injecting a contrast agent into the LAA. In a further embodiment of the disclosed technique, an isolation device and delivery sheath is also included for applying the drug or toxin to the tissue surrounding the ostium of the LAA as well. The delivery sheath holds the isolation device in a contracted form. Once positioned at the ostium of the LAA, the delivery sheath is pulled back thus releasing the isolation device which expands to cover the tissue surrounding the ostium of the LAA. A drug or toxin can then be applied to that tissue for killing it as well and electrically isolating that tissue from the rest of the heart.

In another embodiment of the disclosed technique, the deployment hub includes a drug delivery timed release device for housing a drug or toxin which is only released once endothelialization of the occlusion has occurred. In this embodiment, one end of the deployment hub includes a semi-permeable membrane for enabling a fluid to enter the deployment hub. The other end includes a fluid activated glue-dissolving enzyme which dissolves when sufficient fluid comes in contact with it. The glue-dissolving enzyme covers the end of the occlusion device facing the LAA. The amount of enzyme placed is selected such that the enzyme will dissolve from fluid entering the semi-permeable membrane after sufficient time has passed for endothelialization of the occlusion device.

Reference is now made to FIGS. 2A and 2B, which are schematic illustrations of a first and second embodiment of an LAA occlusion device, generally referenced 100 and 120 respectively, constructed and operative in accordance with an embodiment of the disclosed technique. With reference to FIG. 2A, LAA occlusion device 100 includes a membrane 102, a central deployment hub 104 and a plurality of fixation splines 106. Membrane 102 may be embodied as an impermeable membrane or a semi-permeable membrane. As a semi-permeable membrane, membrane 102 may be semi-permeable in only one direction, thus letting liquids pass through the membrane in only one direction. In the case of membrane 102 being an impermeable membrane, membrane 102 is completely closed such that fluid cannot cross through it. In such a case, the LAA may need to be drained of blood, or at least some of the blood therein before the toxin or drug is injected since otherwise the existing blood volume in the LAA will have nowhere to go. In the case of membrane 102 being a semi-permeable membrane, membrane 102 may have poor semi-permeability. Membrane 102 may have the shape of a parachute, an umbrella, may be circular in shape, may have a balloon shape or may have any shape that approximates the anatomy of the ostium of the LAA. Central deployment hub 104 includes a one-way valve (not shown) as well as a threaded aperture (not shown). Central deployment hub 104 can also be referred to as a deployment port. The one-way valve can be used for injecting a drug or toxin into the LAA once deployed. The one-way valve can be embodied as a perforable yet sealable membrane, a sealable polymer membrane, a membrane with a one-way mechanism and the like. Membrane 102 is constructed as to keep the drug or toxin local to the LAA, thereby effectively killing the tissue of the LAA while not affecting other tissue of the heart. In the case of membrane 102 being a semi-permeable membrane, a small amount of the drug or toxin may seep out of the LAA via the membrane in the case when the drug or toxin is released before endothelialization has occurred. This also enables blood to seep out of the LAA. Even though the drug or toxin may seep out, for example in the case of ethanol being the drug, the drug will mix with the blood in the heart and will end up being diluted thus not causing any damage to the heart outside the LAA. The toxin or drug injected into the LAA however will permeate the LAA undiluted and perform its functions of killing the cells inside the LAA. The threaded aperture enables a catheter or delivery device to be attached to LAA occlusion device 100 for placement in the LAA. Once deployed, the catheter or delivery device can be unscrewed thus leaving the LAA occlusion device in place. Plurality of fixation splines 106 are made from a biocompatible metal and may be designed to have a closed and open shape. Plurality of fixation spines 106 are arranged radially around central deployment hub 104. Plurality of fixation splines 106 are used to position and hold LAA occlusion device 100 in the ostium of the LAA while the natural process of endothelialization occurs. Plurality of fixation splines 106 may also be formed in a spring shape held under pressure by a delivery sheath such that when the delivery sheath is removed, the fixation splines open membrane 102 into an umbrella shape, a parachute shape, a circular shape, a balloon shape or a shape which approximates the anatomy of the ostium of the LAA. In the case of membrane 102 being embodied as a semi-permeable membrane, any blood located in the LAA can seep out of the LAA via the semi-permeable membrane into the LA. This may also be the case when the drug or toxin is released into the LAA before endothelialization occurs, with small amounts of blood mixed with the drug or toxin seeping through the semi-permeable membrane into the LA. If the semi-permeability of membrane 102 in this embodiment is only in one direction, then blood in the LA cannot enter the LAA, however blood and/or the drug or toxin can seep out of the LAA into the LA before endothelialization occurs.

In another embodiment of the disclosed technique the LAA occlusion device may only include a membrane and a central deployment hub, not having any fixation splines. In this embodiment (not shown), other elements may be used to hold the LAA occlusion device in place while the toxin or drug is injected into the LAA. For example, in one embodiment, staples may be used to affix the membrane to the ostium of the LAA. In another embodiment, a glue may be used to affix the membrane to the ostium of the LAA. In yet a further embodiment, a balloon catheter or other type of soft catheter can be inserted behind the LAA occlusion device and inflated once the LAA occlusion device is in place, thereby holding the LAA occlusion device at the ostium of the LAA while the drug or toxin is injected into the LAA.

With reference to FIG. 2B, LAA occlusion device 120 includes a semi-permeable membrane 122, a central deployment hub 124 and a plurality of fixation splines 126. Semi-permeable membrane 122 may allow small amounts of fluid to cross it, thus once positioned in the ostium of the LAA, semi-permeable membrane 122 may allow blood to cross from the LAA to the LA and vice-versa, however any blood clots formed in the LAA will remain there. Semi-permeable membrane 122 may be designed as a very fine sieve. All other aspects of LAA occlusion device 120 are identical to LAA occlusion device 100.

In either LAA occlusion device, a catheter or delivery tube can be coupled with (for example, screwed into the threaded aperture) the central deployment hub for injecting a drug, toxin, medication or therapeutic agent into the LAA for killing the cardiac tissue of the LAA. A possible drug which can be used to kill the tissue of the LAA is ethanol mixed with X-ray contrast. In general, ethanol is toxic to cardiac tissue in high concentrations, thus a high concentration of ethanol should be injected into the LAA to kill the tissue. However in lower concentrations, ethanol is not toxic to cardiac tissue. Therefore, if ethanol leaks out of the LAA into the LA and the heart and the blood stream, the flow of blood into the heart should dilute the ethanol to concentrations which are not toxic to the patient. As mentioned above, the drug or toxin can be any biological inhibitor of cellular function, such as a drug, a medication, a viral vector and the like.

Reference is now made to FIG. 3, which is a schematic illustration of an isolation device and a delivery sheath, generally referenced 150, constructed and operative in accordance with another embodiment of the disclosed technique. FIG. 3 shows an injection tube 152, an isolation device 154 and a delivery sheath 156. Injection tube 150 can be used for injecting a drug or toxin into the LAA via the occlusion devices shown in FIGS. 2A and 2B. Injection tube 150 can also be used for injecting a drug or toxin into the tissue around the ostium of the LAA. Isolation device 154 is an expandable membrane which is held in place by delivery sheath 156. Isolation device 154 may be embodied as a filter basket or sheath, similar to the impermeable or semi-permeable membranes of the LAA occlusion devices shown in FIGS. 2A and 2B. Isolation device 154 and delivery sheath 156 may be deployed via the same delivery system used to deploy the LAA occlusion device of FIGS. 2A and 2B into the region of the antrum or vestibule of the area around the LAA.

Isolation device 154 includes an expandable section 160 which is held flush against the inner edges of delivery sheath 156, as shown by an arrow 158. Edges 162 of isolation device 154 may include grips, suction bulbs or other mechanisms (not shown) for temporarily coupling isolation device 154 with the tissue surrounding the ostium of the LAA. After deployment of the LAA occlusion device, isolation device 154 and delivery sheath 156 may be deployment over the LAA occlusion device. Delivery sheath 156 is then pulled back, enabling isolation device 154 to expand and substantially cover the tissue surrounding the ostium of the LAA.

In one embodiment of the disclosed technique, isolation device 154 is used to ensure that any drug or toxin applied to the LAA which might leak out does not enter the LA, the heart or the circulatory system. In another embodiment of the disclosed technique, once isolation device is deployed, injection tube 152 may be pulled back slightly such that the drug and toxin can be applied to the tissue around the ostium of the LAA by filling up the lumen formed by the isolation device. Isolation device 154 thus ensures that the injected drug or toxin does not enter the LA or the heart or blood stream. After the toxin has destroyed the tissue surrounding the ostium of the LAA, which may take about 10-15 minutes, injection tube 152 can be removed and a vacuum tube can be inserted to vacuum out the drug or toxin before delivery sheath 156 and isolation device 154 are removed.

Figure 4:
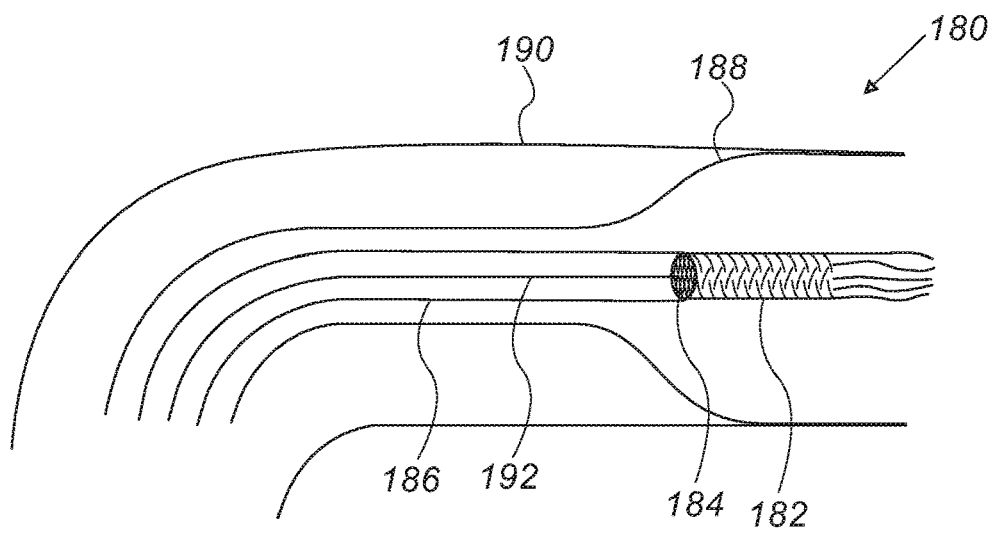
FIG. 4 is a schematic illustration of an LAA occlusion system, constructed and operative in accordance with a further embodiment of the disclosed technique.

Reference is now made to FIG. 4, which is a schematic illustration of an LAA occlusion system, generally referenced 180, constructed and operative in accordance with a further embodiment of the disclosed technique. LAA occlusion system 180 includes an LAA occlusion device 182, an injection tube 186, an isolation device 188 and a delivery sheath 190. LAA occlusion device 182 is coupled with injection tube 186 via a threaded aperture 184 in occlusion device 182. In another embodiment of the disclosed technique (not shown), LAA occlusion device 182 may be coupled with injection tube 186 via a glue, staples or via an inflated balloon catheter and not via a threaded aperture. LAA occlusion device 182 can be either one of LAA occlusion devices 100 (FIG. 2A) or 120 (FIG. 2B) and is shown in FIG. 4 in a contracted state. Isolation device 188 and delivery sheath 190 are substantially similar to the isolation device and delivery sheath shown above in FIG. 3. A guidewire 192 may be used initially to locate the ostium of the LAA after which the other elements of LAA occlusion system 180 are deployed to the LAA.

Figure 5A:
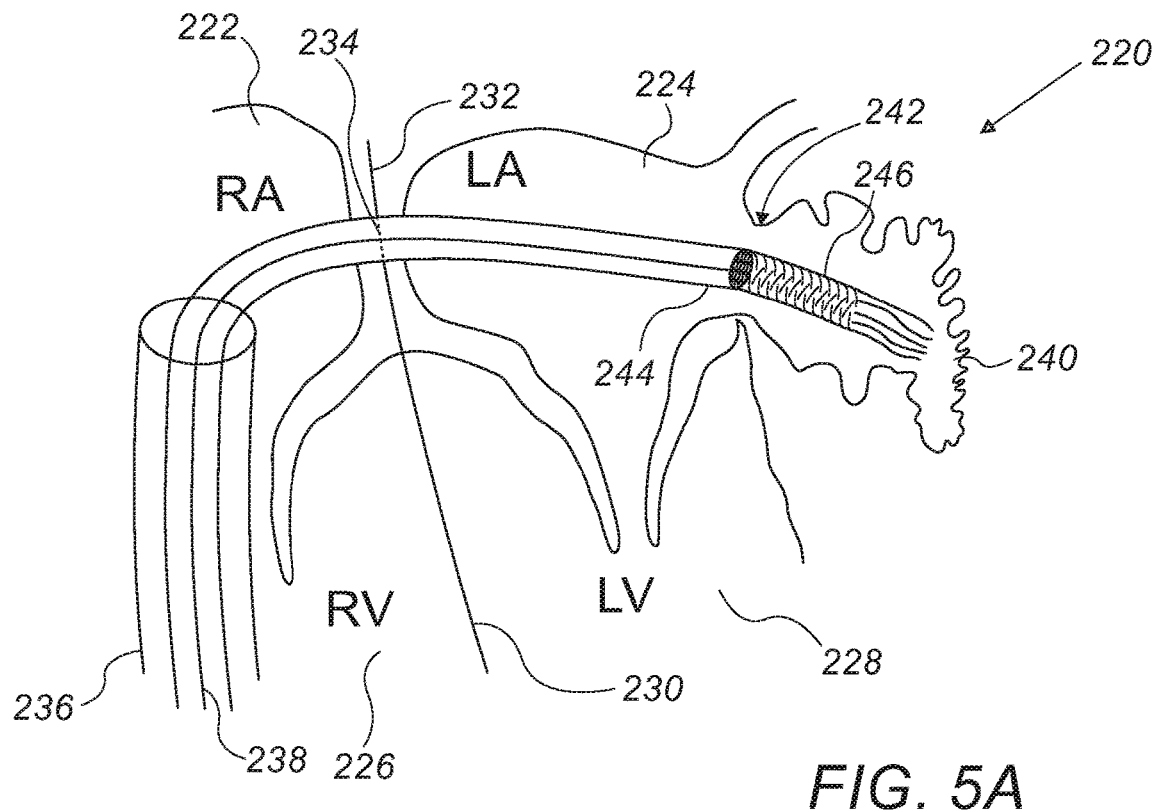
FIGS. 5A-5F are schematic illustrations of the deployment of the LAA occlusion system of FIG. 4 in a patient, constructed and operative in accordance with another embodiment of the disclosed technique.

Reference is now made to FIGS. 5A-5F, which are schematic illustrations of the deployment of the LAA occlusion system of FIG. 4 in a patient, generally referenced 220, constructed and operative in accordance with another embodiment of the disclosed technique. Identical elements in these figures are labeled using identical reference numbers. Not all elements are labeled in every figure in order to keep the figures from being too cluttered. With reference to FIG. 5A, shown is a section of the heart, including an RA 222, an RV 226, an LA 224 and an LV 228. A septum 230 separates the left side and right side of the heart. Shown as well is an LAA 240, an inferior vena cava 236 which leads into RA 222, an interatrial septum 232 and a fossa ovalis 234. The entrance or ostium of LAA 240 is shown via an arrow 242. A guidewire 238 is inserted into a patient via the right femoral vein (not shown) or other blood vessel which links up with inferior vena cava 236, thus gaining access to RA 222. Guidewire 238 is used to puncture fossa ovalis 234, or at another transseptal puncture point, thus enabling access to LA 224 and LAA 240. An injection tube 244, loaded with an LAA occlusion device 246 of the disclosed technique, is then moved over guidewire 238 until LAA occlusion device 246 is within LAA 240.

Figure 5B:
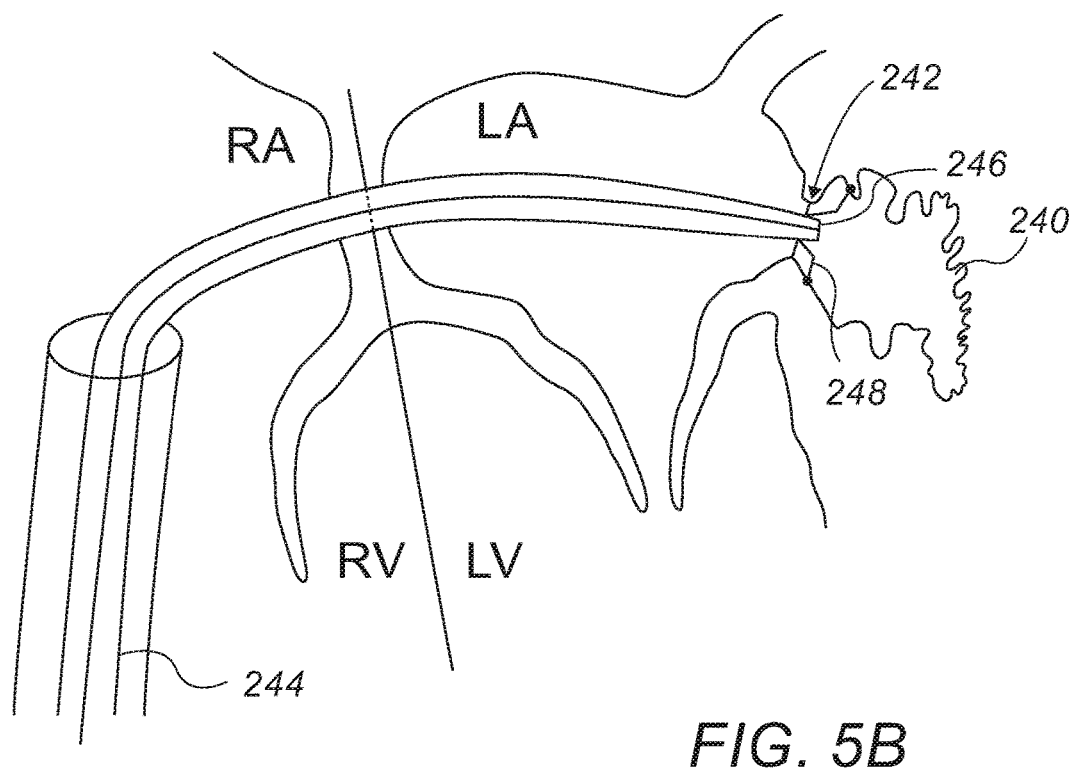
Figure 5D:
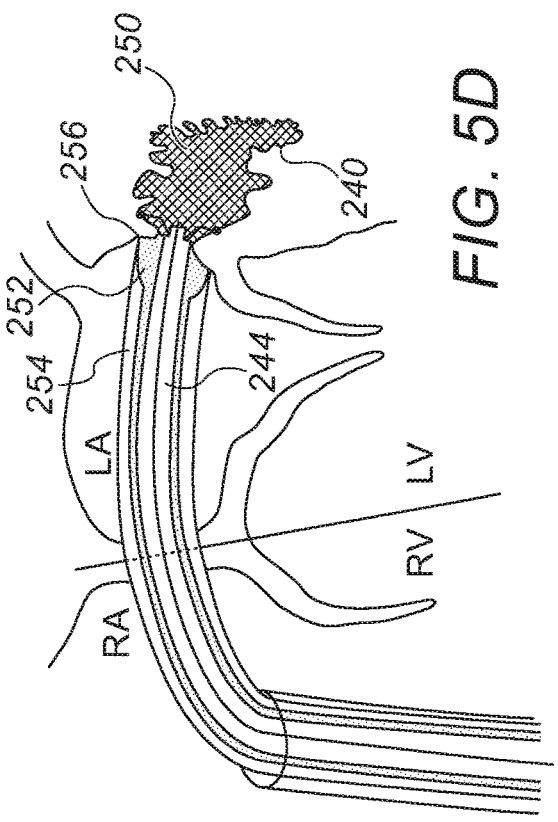
Figure 5F:
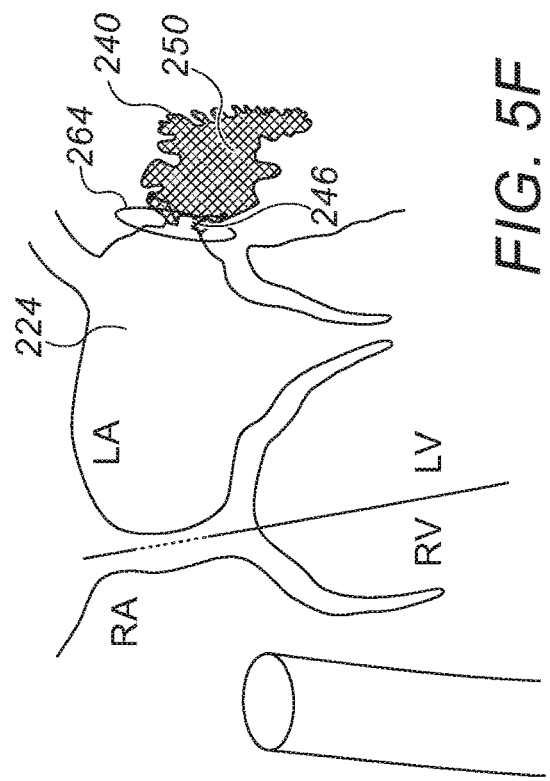
Figure 5C:
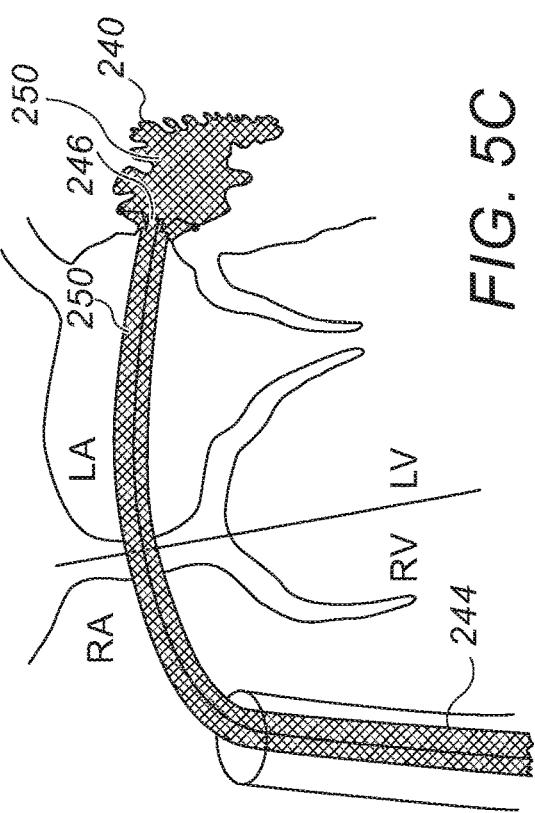
Figure 5E:
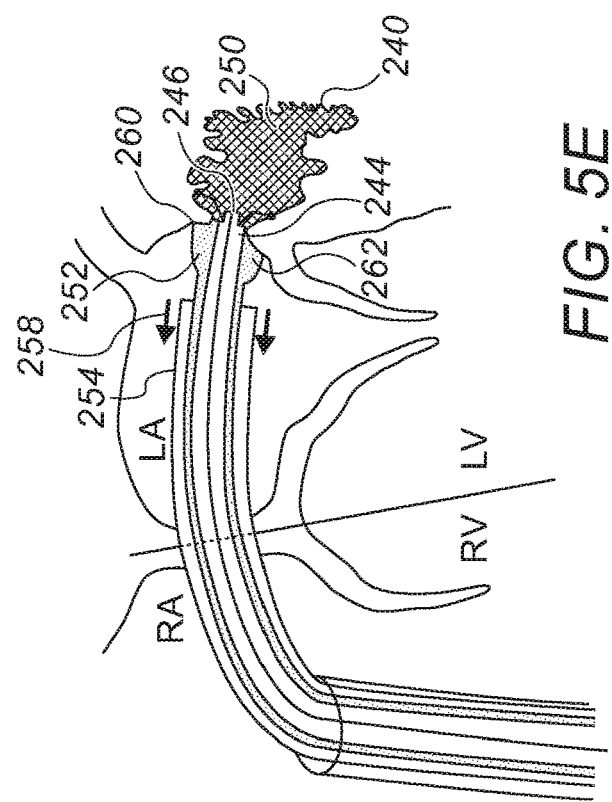

With reference to FIG. 5B, LAA occlusion device 246 is deployed such that a plurality of fixation splines 248 affix LAA occlusion device 246 to the tissue forming the ostium of LAA 240. With reference to FIG. 5C, once properly deployed and firmly in place, a drug, toxin, therapeutic agent or medication 250 is injected via injection tube 244 into LAA 240. Drug 250 is injected into LAA 240 via the one-way valve (not shown) of LAA occlusion device 246. Once injected, drug 250 kills the tissue of LAA 240 such that it is no longer electrically active, thus elimination LAA 240 as a source of AF in certain patients. As mentioned above, this may take between 10-15 minutes. With reference to FIG. 5D, an isolation device 252 and a delivery sheath 254 are inserted over injection tube 244 and positioned around the tissue surrounding the ostium of LAA 240. Isolation device 252 and delivery sheath 254 are positioned around the ostium of LAA 240, shown by a reference line 256. With reference to FIG. 5E, delivery sheath 254 is pulled back, as shown by a plurality of arrows 258 such that the expandable section (not labeled) of isolation device 252 expands around the tissue at the ostium of LAA 240, shown by a reference line 260. Isolation device 252 is then temporarily coupled with the area around the antrum or vestibule of LAA 240. Studies have shown that when the LAA is a source of AF, the tissue surrounding the ostium of the LAA can also be a source of AF. Therefore according to the disclosed technique, injection tube 244 is released from LAA occlusion device 246 (not shown) and drug 250 is released (not shown) into a lumen 262 formed by isolation device 252 to kill the tissue surrounding the ostium of the LAA as well. As mentioned above, injection tube 244 may then be removed and a suction tube or vacuum tube (both not shown) may be inserted to remove drug 250 from lumen 262. With reference to FIG. 5F, once the drug has been removed from the lumen formed by the isolation device, the delivery sheath, isolation device, injection tube and guidewire are removed, leaving LAA occlusion device 246 in place covering LAA 240. Within a few weeks, LAA occlusion device 246 with be covered with endothelial cells through the body's natural process of endothelialization, thus permanently leaving LAA occlusion device 246 at the ostium of LAA 240 and preventing the further formation of blood clots. As a toxin was inserted into LAA 240 to kill the cardiac tissue therein, LAA 240 is not just physically separated but also electrically isolated from LA 224, thus ceasing to be a source of AF. A region 264 of cardiac tissue surrounding the ostium of LAA 240 has also been killed by the toxin, thus also ceasing to be a source of AF in certain patients.

FIGS. 5A-5F have shown one embodiment of the deployment of the LAA occlusion system of the disclosed technique. Other deployments are possible. For example, a balloon catheter can be used to keep the LAA occlusion device held in place while the toxin is injected into the LAA, wherein the LAA occlusion device does not include a plurality of fixation splines. As another example, injection tube 244 may be used to release a glue at the ostium of the LAA for gluing the LAA occlusion device to the ostium of the LAA before the toxin or drug is released into the LAA. In such an embodiment, the LAA occlusion device also does not include or require a plurality of fixation splines.

Figure 6A:
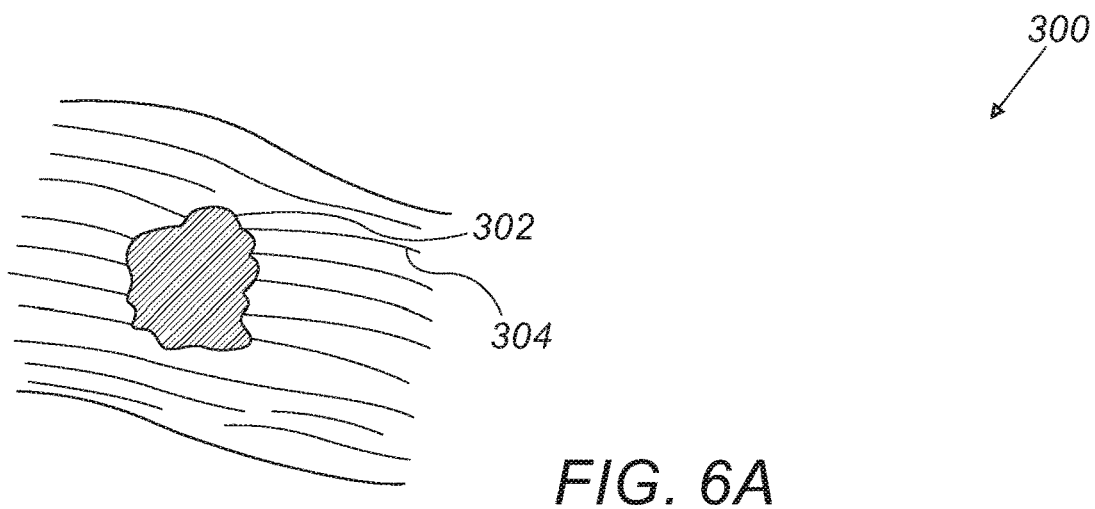
FIGS. 6A-6C are top views of the ostium of the LAA during different stages of the deployment of the LAA occlusion system of FIG. 4, constructed and operative in accordance with a further embodiment of the disclosed technique.
Figure 6B:
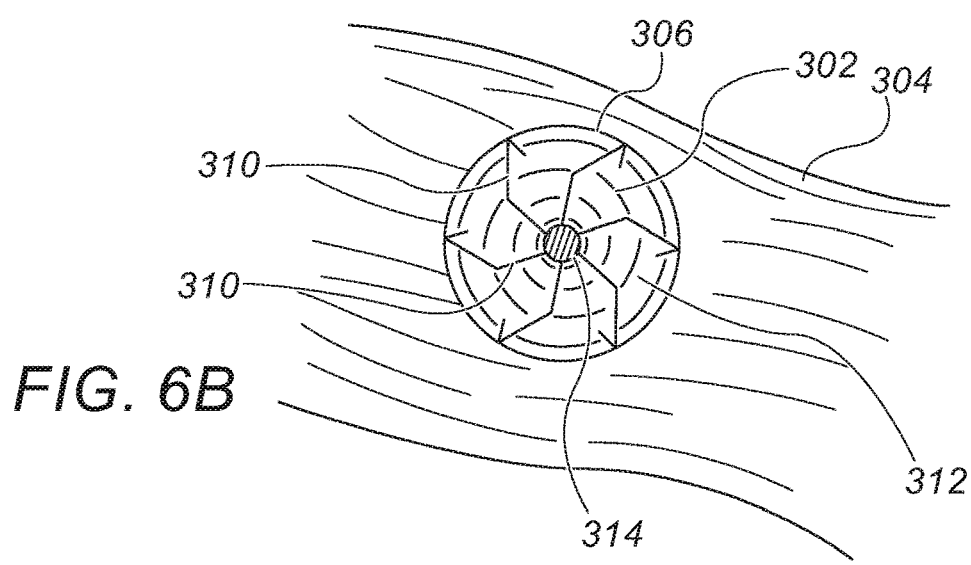
Figure 6C:
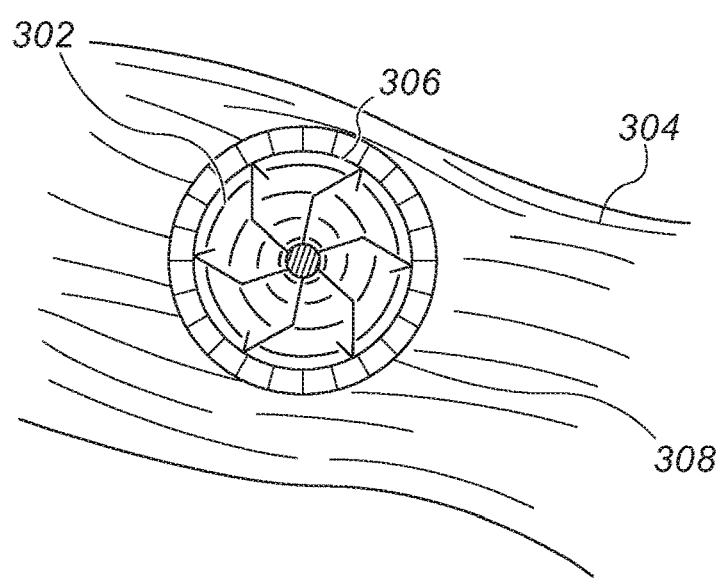

Reference is now made to FIGS. 6A-6C, which are top views of the ostium of the LAA during different stages of the deployment of the LAA occlusion system of FIG. 4, generally referenced 300, constructed and operative in accordance with a further embodiment of the disclosed technique. Identical elements in these figures are labeled using identical reference numbers. With reference to FIG. 6A, shown is a top view of the ostium of an LAA 302 and the wall of an LA 304. With reference to FIG. 6B, shown is a top view of an LAA occlusion device 306 of the disclosed technique placed over the ostium of LAA 302. Shown is the deployment of a plurality of fixation splines 310, a semi-permeable membrane 312 covering the entire ostium of LAA 302 and a central deployment hub 314 having a one-way valve and a threaded aperture. With reference to FIG. 6C, shown is a top view of LAA occlusion device 306 deployed along with the deployment of an isolation device 308. As can be seen, isolation device 308 covers a larger surface area than LAA occlusion device 306 such that not only the tissue of the LAA can be killed by a drug or toxin but also the area surrounding the ostium of the LAA.

Figure 7A:
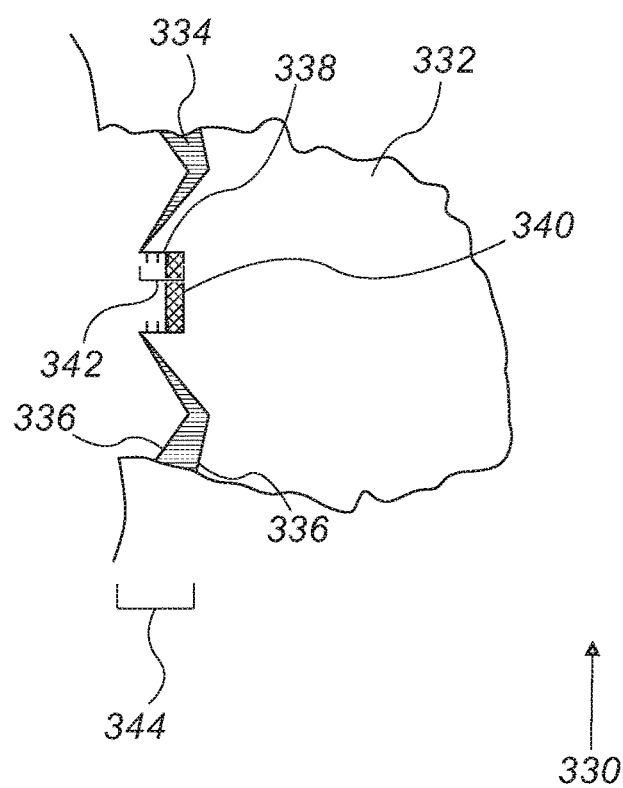
FIGS. 7A and 7B are schematic illustrations of the LAA occlusion device of FIGS. 2A and 2B being deployed at different positions within the LAA, constructed and operative in accordance with another embodiment of the disclosed technique.
Figure 7B:
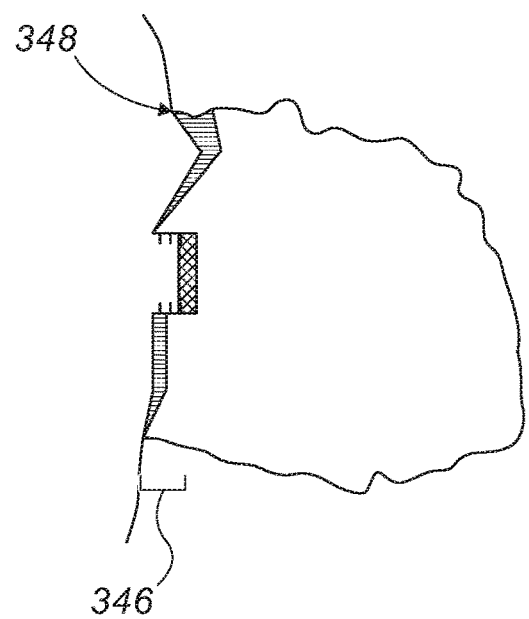

Reference is now made to FIGS. 7A and 7B, which are schematic illustrations of the LAA occlusion device of FIGS. 2A and 2B being deployed at different positions within the LAA, generally referenced 330, constructed and operative in accordance with another embodiment of the disclosed technique. A close-up view of the LAA occlusion device of the disclosed technique is shown positioned inside an LAA 332. Shown in greater detail is a semi-permeable membrane 334, a plurality of fixation splines 336, a central deployment hub 338 including a one-way valve 340 as well as a threaded aperture 342. As shown in FIG. 7A, plurality of fixation splines 336 can be positioned such that the LAA occlusion device is within LAA 332, as shown by a section 344. With reference to FIG. 7B, which shows the same LAA occlusion device, however positioned slightly differently, the plurality of fixation splines can be positioned right at the ostium of the LAA, as shown by a section 346. As shown by an arrow 348, LAA occlusion device now covers the ostium of LAA 332.

Figures 8A, 8B:
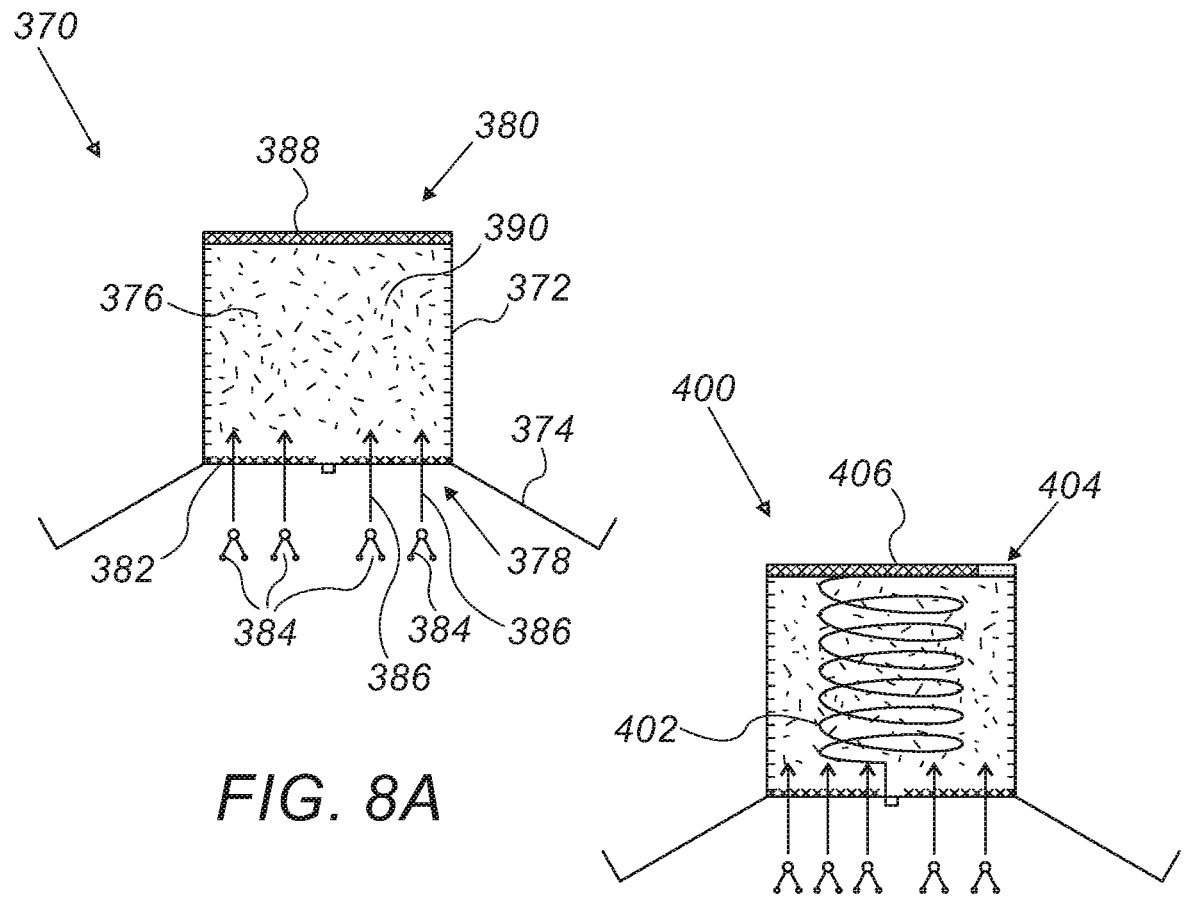
FIGS. 8A and 8B are schematic illustrations of the drug delivery mechanism of the LAA occlusion device of FIGS. 2A and 2B, constructed and operative in accordance with a further embodiment of the disclosed technique.

Reference is now made to FIGS. 8A and 8B, which are schematic illustrations of the drug delivery mechanism of the LAA occlusion device of FIGS. 2A and 2B, generally referenced 370 and 400 respectively, constructed and operative in accordance with a further embodiment of the disclosed technique. FIG. 8A shows a first embodiment of the drug delivery mechanism of the disclosed technique. As shown is a central deployment hub 372 of an LAA occlusion device, which includes a plurality of fixation splines 374. Deployment hub 372 is filled with a target drug, toxin, therapeutic agent or medication 376 as well as a fluid activated glue-dissolving enzyme 390. Target drug 376 is placed in the lumen of deployment hub 372 as a dry substance. A partial vacuum may also be applied to the lumen. Deployment hub 372 has a proximal end 378 facing the LA as well as a distal end 380 facing the LAA. Proximal end 378 is covered with a molecular sieve 382 which allows fluids, shown as a plurality of particles 384, to cross from the LA into the lumen of deployment hub 372, shown by a plurality of arrows 386. The fluid may be blood, water or other fluids normally found in the body. Distal end 380 is covered with a glue 388. Glue 388 is substantially impermeable until glue-dissolving enzyme 390 comes in contact with it. Glue 388 may be made from a biological agent which is subject to enzymatic degradation by glue-dissolving enzyme 390. Glue-dissolving enzyme 390 only becomes activated when sufficient fluid comes into contact with it. When sufficient amounts of particles 384 (i.e., the fluid) come into contact with glue-dissolving enzyme 390, the particles react with the enzyme which begins to dissolve glue 388 and allows particles to pass there through. The rate at which glue 388 dissolves is a function of a number of factors such as the concentration of the enzyme in deployment hub 372, how quickly molecular sieve 382 allows fluid to enter the lumen of deployment hub 372 and the chemistry of glue 388 and glue-dissolving enzyme 390. Adjusting these factors, the release of target drug 376, via the loss of adhesion of glue 388, can be tailored for specific time-release periods, thus enabling target drug 376 to be time-released.

Considering it takes about 4 weeks for endothelial cells to cover an LAA occlusion device, the described time-release factors of deployment hub 372 can be selected such that glue-dissolving enzyme 388 will dissolve after approximately 6 weeks, thus releasing the target drug into the LAA to kill the tissue therein. An example of a target drug may be doxorubicin (sold under the trade name Adriamycin® or Rubex®), which has a high molecular weight and is also toxic to cardiac tissue. As mentioned above, drug delivery of the target drug is activated by fluid or moisture coming into contact with the fluid activated glue-dissolving enzyme. Once the LAA occlusion device is employed, fluid passing through molecular sieve 382 will start activating glue-dissolving enzyme 390 which will begin dissolving glue 388 and slowly allowing target drug 376 to enter the LAA. As mentioned above, the factors determining when glue 388 dissolves can be adjusted such that the target drug is only released after endothelialization of the ostium of the LAA. In this embodiment of the disclosed technique, the cardiac tissue of the LAA is killed once the LAA occlusion device is deployed and fully covered by endothelial cells. As such, the LAA occlusion device is deployed and within a number of weeks of deployment, the LAA will begin to deteriorate and lose function.

Reference is now made to FIG. 8B, which shows another embodiment of the drug delivery mechanism of the disclosed technique. In this embodiment, the deployment hub includes a spring 402 and a lid 406. Lid 406 is coupled with the deployment hub by a glue 404 at only one section of lid 406. This embodiment is substantially similar to the embodiment shown in FIG. 8A in terms of elements (not labeled) and function, except that once glue 404 is dissolved, spring 402, which may be loaded into the deployment hub under pressure, pushes lid 406 open, thus enabling the target drug to enter into the endoluminal appendage space and start deteriorating the cardiac cells of the LAA.

It is noted that the drug delivery mechanism of the disclosed technique has been described relating to timed drug release in the LAA, however the drug delivery mechanism of the disclosed technique may be used in other procedures and in other locations in the body for timed drug release.

Figure 9A:
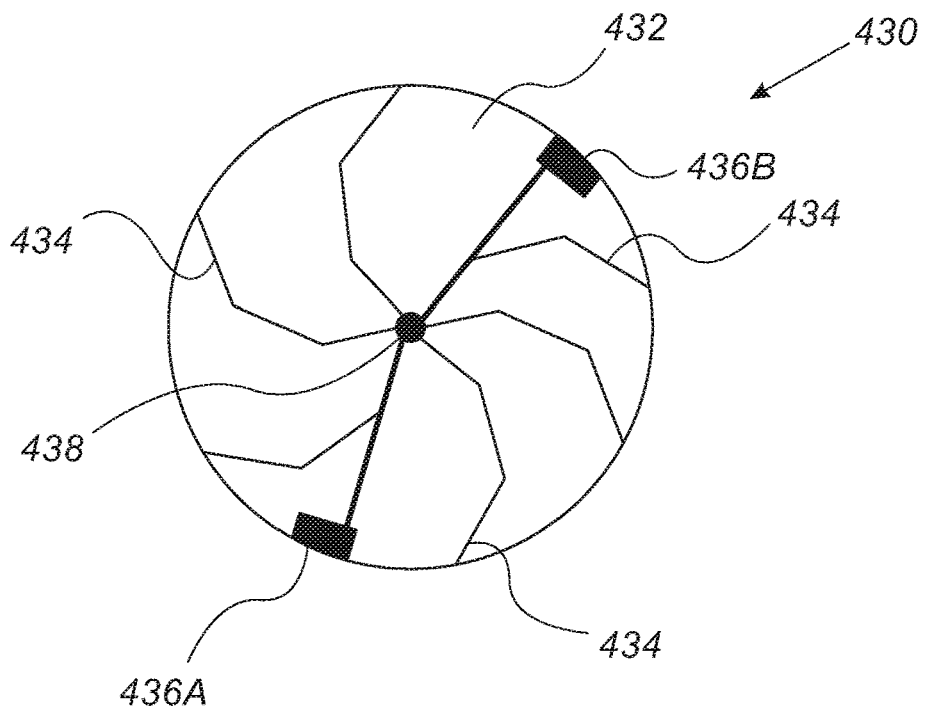
FIG. 9A is a schematic illustration of a third embodiment of an LAA occlusion device, constructed and operative in accordance with another embodiment of the disclosed technique.

Reference is now made to FIG. 9A, which is a schematic illustration of a third embodiment of an LAA occlusion device, generally referenced 430, constructed and operative in accordance with another embodiment of the disclosed technique. LAA occlusion device 430 includes a membrane 432, a plurality of fixation splines 434, at least two electrical conductors 436A and 436B and an interconnect 438. Membrane 432 may be embodied as an impermeable membrane or a semi-permeable membrane as described above in FIGS. 2A and 2B. As a semi-permeable membrane, membrane 432 may be semi-permeable in only one direction, thus letting liquids pass through the membrane in only one direction. Plurality of fixation splines 434 is coupled with interconnect 438. Electrical conductors 436A and 436B are also coupled with interconnect 438. Plurality of fixation splines 434 is similar to plurality of fixation splines 106 (FIG. 2A) and plurality of fixation splines 126 (FIG. 2B) as described above. Plurality of fixation splines 434 and electrical conductors 436A and 436B may be interweaved or coupled with membrane 432. As described above in FIG. 4, LAA occlusion device 430 may be have an expanded state (as shown) and a contracted state (not shown). The contracted state has plurality of fixation splines 434 and electrical conductors 436A and 436B folded up with membrane 432 such that LAA occlusion device 430 can be inserted through the vasculature of a patient to the ostium of the LAA. The expanded state opens up membrane 432 such that it covers and substantially blocks the ostium of the LAA. Electrical conductors 436A and 436B can be made from any biocompatible conductor material, such as titanium or Nitinol.

LAA occlusion device 430 may optionally include a central deployment hub (not shown), similar to what was shown above in FIGS. 2A, 2B, 8A and 8B. The central deployment hub would be located where interconnect 438 is located and would couple plurality of fixation splines 434 and electrical conductors 436A and 436B as well as enabling a liquid or contrast agent to be inserted there through into the LAA. In this embodiment, the central deployment hub would be used to insert a contrast agent into the LAA for aiding in imaging the LAA while LAA occlusion device 430 is deployed. Membrane 432 would then be embodied as a semi-permeable membrane, thereby allowing the contrast agent to eventually diffuse out of the LAA while not allowing any blood clots or thrombi which form in the LAA to leave.

In the embodiment of FIG. 9A, once LAA occlusion device 430 is deployed and plurality of fixation splines 434 have been expanded such that membrane 432 covers the ostium of the LAA, electrical conductors 436A and 436B may be coupled with a DC or AC source of electricity via interconnect 438 for providing high voltage DC or AC electricity (or any of kind of phased current electrical energy) between electrical conductors 436A and 436B. The electric energy source may also be coupled with plurality of fixation splines 434 for providing high voltage DC or AC electricity between various pairs of fixation splines (shown below in FIGS. 9C and 9D). According to one embodiment of the disclosed technique, once LAA occlusion device 430 is deployed, but before a guidewire and an injection tube used to deploy the LAA occlusion device are removed from the patient, an electrical wire is inserted through the injection tube to couple the electrical conductors with a source of electricity. According to the disclosed technique, since cardiomyocytes (i.e., cardiac muscle cells) have a cell membrane that is highly charged electrically, cardiomyocytes in the rim of the ostium of the LAA can be preferentially electrocuted with the application of high voltage electricity (DC or AC) between electrical conductors 436A and 436B. The technique of passing high voltage electricity between two conductors to disrupt or kill cells is known as electroporation. According to the disclosed technique, electroporation is used with electrical conductors 436A and 436B to disrupt the cell membrane of cardiomyocytes in the rim of the ostium of the LAA thus effectively killing the heart tissue in the rim of the ostium of the LAA and electrically isolating the LAA from the rest of the heart. With the heart tissue in the ostium of the LAA being destroyed by the LAA occlusion device of the disclosed technique, the LAA is not only physically isolated from the LA but is also electrically isolated from the rest of the heart.

According to the disclosed technique, once the rim of the ostium of the LAA is electroporated, the electrical wire is removed along with the injection tube and the guidewire, thus leaving an LAA which is covered and blocked and also electrically isolated from the rest of the heart. The disclosed technique allows for electroporation without heating any heart tissue in the process. Other techniques, such as radio frequency (herein abbreviated RF) ablation, could be used to electrocute the rim of the ostium of the LAA, but such techniques required a ground patch to be placed on the surface of the skin of the patient and for AC electricity to be passed from the ground patch to a conductor placed near the LAA. The passing of AC electricity in the RF range will cause any tissue between the ground patch and the conductor to heat up and possibly cause unwanted tissue damage in the skin and other tissue layers between the ground patch and the conductor. According to the disclosed technique, electroporation using electrical conductors 436A and 436B does not require a ground patch, does not require AC electricity in the RF range and thus does not cause any tissue to substantially heat up to a point which could cause tissue damage. Since the cell membrane of cardiomyocytes is highly charged electrically, such cells are preferentially disrupted and killed by the application of an electric current as opposed to other types of tissues. LAA occlusion device 430 may include a plurality of electrical conductors (not shown) which may also be electrically coupled with plurality of fixation splines 434 for providing sufficient electrical current to electroporate the cardiomyocytes in the rim of the ostium of the LAA.

According to the disclosed technique, the cardiac cells in the LAA do not need to be killed in their entirety to isolate the LAA electrically from the rest of the heart. By electrically isolating just the rim of the ostium of the LAA according to the disclosed technique, the LAA will by electrically isolated from the LA and the rest of the heart and the conduction of atrial fibrillation from the LAA into the LA will be prevented.

According to another embodiment of the disclosed technique as described below in greater detail in FIGS. 9C and 9D, LAA occlusion device 430 does not include independent electrical conductors 436A and 436B as shown but instead has electrical conductors coupled with interconnect 438 for applying high voltage DC or AC electricity through plurality of fixation splines 434 into the cardiac tissue in the rim of the ostium of the LAA. In this embodiment, plurality of fixation splines 434 is a plurality of conductive fixation splines for conducting electrical current. In this embodiment, an electrical wire (not shown) is coupled with interconnect 438 when LAA occlusion device 430 is deployed. Once plurality of fixation splines 434 are expanded and physically isolate the LAA, electrical current is applied through the electrical wire to the plurality of fixation splines via the interconnect for electroporating the rim of the ostium of the LAA. Once electroporation has occurred, the electrical wire is removed along with the injection tube and guidewire used to initially deploy the LAA occlusion device. The electrical connection of the electrical wire with the interconnect may be frangible such that when the injection tube and guidewire are removed, the electrical wire easily severs its connection with the interconnect.

Figure 9B:
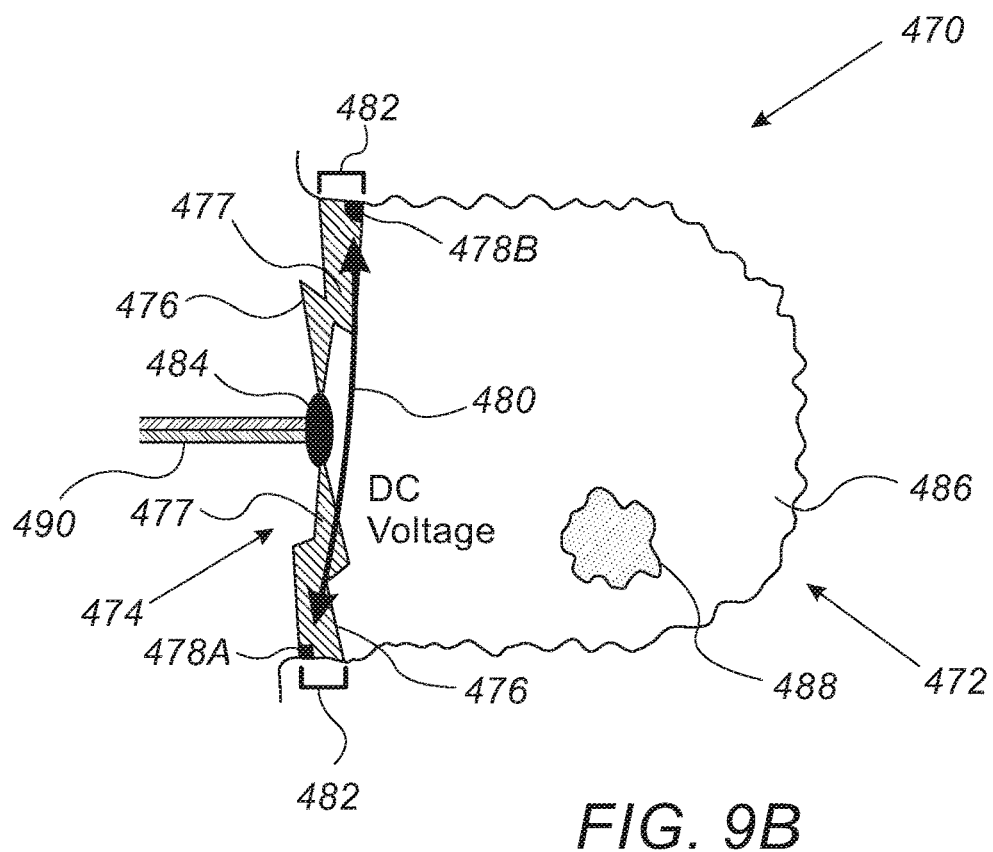
FIG. 9B is a schematic illustration of the LAA occlusion device of FIG. 9A being deployed within the LAA, constructed and operative in accordance with a further embodiment of the disclosed technique.

Reference is now made to FIG. 9B, which is a schematic illustration of the LAA occlusion device of FIG. 9A being deployed within the LAA, generally referenced 470, constructed and operative in accordance with a further embodiment of the disclosed technique. FIG. 9B shows an LAA occlusion device 474 (such as described above in FIG. 9A) deployed in an LAA 472. LAA occlusion device 474 includes a plurality of fixation splines 476, a membrane 477, at least two electrical conductors 478A and 478B as well as an interconnect 484 and an electrical wire 490 coupled with fixation point 484.

Electrical wire 490 applies high voltage DC or AC electricity to interconnect 484 which then transfers the electricity to electrical conductors 478A and 478B. As shown for example, a DC voltage vector 480 passes between electrical conductors 478A and 478B, thereby electroporating the rim of the ostium of LAA 472, shown by a section 482. By electrocuting the cardiomyocytes in section 482, the rest of the LAA is electrically isolated from the LA and the other chambers and parts of the heart (not shown). Once sufficient electricity has been applied to the rim of the ostium of LAA 472, electrical wire 490 is removed. As shown, plurality of fixation splines 476 along with membrane 477 physically isolate an inner space 486 of LAA 472 from the rest of the heart thus preventing blood clots and thrombi, such as blood clot 488, from leaving LAA 472 and entering the vasculature of a patient.

Figure 9C:
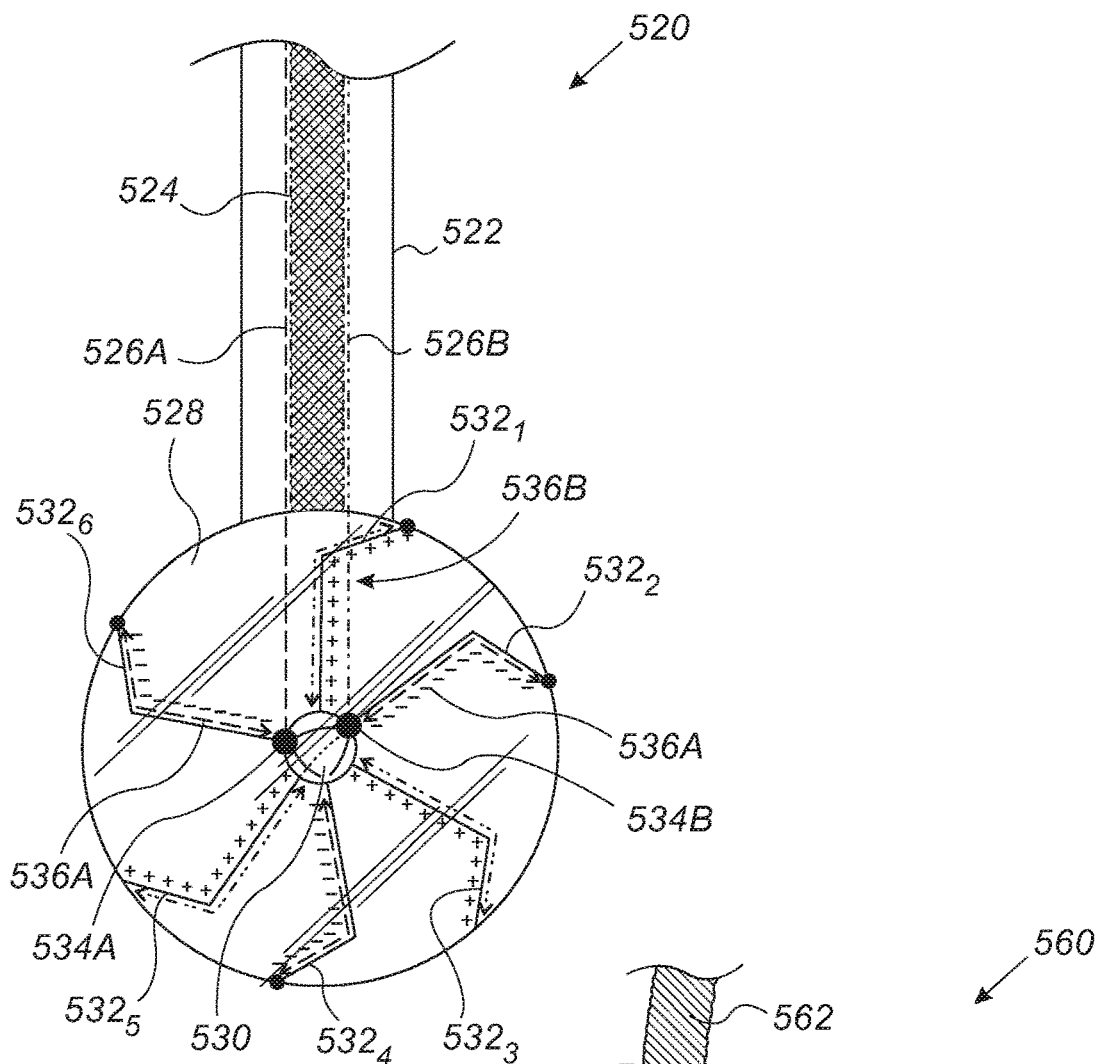
FIG. 9C is a schematic illustration of a fourth embodiment of an LAA occlusion device, constructed and operative in accordance with a another embodiment of the disclosed technique.

Reference is now made to FIG. 9C, which is a schematic illustration of a fourth embodiment of an LAA occlusion device, generally referenced 520, constructed and operative in accordance with another embodiment of the disclosed technique. LAA occlusion device 520 is similar to LAA occlusion device 430 (FIG. 9A) except that instead of having electrical conductors positioned between the fixation splines (as in FIG. 9A), LAA occlusion device 520 uses the fixation splines as the electrical conductors. LAA occlusion device 520 includes a delivery shaft 522, an injection tube 524, a negative electrical current conductor 526A, a positive electrical current conductor 526B, a membrane 528, an interconnect 530 and a plurality of conductive fixation splines 532$_1$-532$_6$. Delivery shaft 522 may be embodied like delivery sheath 254 (FIG. 5D). Injection tube 524 may be embodied like injection tube 152 (FIG. 3). Negative electrical current conductor 526A and positive electrical current conductor 526B are substantially coupled with injection tube 524 and run along the length of the injection tube. Negative electrical current conductor 526A is shown as a dashed line whereas positive electrical current conductor 526B is shown as a dash-dash-dot-dot line. Membrane 528 is substantially similar to membrane 102 (FIG. 2A) and may be semipermeable or impermeable. Interconnect 530 is substantially similar to interconnect 438 (FIG. 9A). Plurality of conductive fixation splines 532$_1$-532$_6$ is similar to plurality of fixation splines 434 (FIG. 9A) and can conduct DC, AC or phased electrical current. Plurality of conductive fixation splines 532$_1$-532$_6$ can be made from a biocompatible conductor material, such as from titanium or Nitinol. As shown, injection tube 524, negative electrical current conductor 526A and positive electrical current conductor 526B are all coupled with interconnect 530 as is plurality of conductive fixation splines 532$_1$-532$_6$. Injection tube 524, negative electrical current conductor 526A and positive electrical current conductor 526B may be detachable from interconnect 530 and may have a frangible design such that sufficient force severs the connection between injection tube 524, negative electrical current conductor 526A and positive electrical current conductor 526B with interconnect 530 while still leaving the plurality of conductive fixation splines coupled with and covering the ostium (not shown) of an LAA of a patient (not shown). Injection tube 524, negative electrical current conductor 526A and positive electrical current conductor 526B may also be coupled with interconnect 530 via a threaded aperture (not specifically shown) such that injection tube 524, negative electrical current conductor 526A and positive electrical current conductor 526B can be attached and detached from interconnect 530 by screwing or unscrewing. As shown, negative electrical current conductor 526A is coupled with interconnect 530 via a negative terminal 534A on interconnect 530 and positive electrical current conductor 526B is coupled with interconnect 530 via a positive terminal 534B on interconnect 530. Select ones of plurality of conductive fixation splines 532$_1$-532$_6$ are electrically coupled with negative terminal 534A while other ones of plurality of conductive fixation splines 532$_1$-532$_6$ are electrically coupled with positive terminal 534B. As shown, plurality of conductive fixation splines 532$_2$, 532$_4$ and 532$_6$ are electrically coupled with negative terminal 534A whereas plurality of conductive fixation splines 532$_1$, 532$_3$ and 532$_5$ are electrically coupled with negative terminal 534B. The proximal ends of negative electrical current conductor 526A and positive electrical current conductor 526B (which are outside the patient when LAA occlusion device 520 is deployed) may be coupled with a high voltage source of electricity, such as a high voltage DC source or a high voltage AC source. It is noted that interconnect 530 may optionally also be embodied as a deployment hub as described above in FIG. 2A, for injecting a contrast agent or drug into the LAA (not shown). It is noted that according to the disclosed technique, at least one of the plurality of conductive fixation splines is coupled with negative electrical current conductor 526A and at least another one of the plurality of conductive fixation splines is coupled with positive electrical current conductor 526B. Thus not all the conductive fixation splines need to be electrically coupled with the electrical current conductors. In FIG. 9C, all the conductive fixation splines are electrically coupled with the electrical current conductors however this is merely an example.

LAA occlusion device 520 is deployed in the LAA of a patient (not shown) in a manner similar to LAA occlusion device 430 (FIG. 9A). Once deployed, the proximal ends of negative electrical current conductor 526A and positive electrical current conductor 526B are coupled with the high voltage source of electricity and a high voltage current is applied via negative electrical current conductor 526A and positive electrical current conductor 526B to plurality of conductive fixation splines 532$_1$-532$_6$. As shown, a negative current is applied to plurality of conductive fixation splines 532$_2$, 532$_4$ and 532$_6$, shown by double-headed arrows and '−' signs 536A. Likewise, a positive current is applied to plurality of conductive fixation splines 532$_1$, 532$_3$ and 532$_5$, shown by double-headed arrows and '+' signs 536B. The high voltage current is applied for approximately 5 to 20 seconds to disrupt the cardiomyocytes via electroporation and without significant tissue heating in the rim (not shown) of the ostium of the LAA, thereby killing those heart cells and electrically isolating the LAA from the LA of the patient. As mentioned above, injection tube 524, negative electrical current conductor 526A and positive electrical current conductor 526B can be detached from interconnect 530 thereby leaving membrane 528 and plurality of conductive fixation splines 532$_1$-532$_6$ in position and physically isolating the LAA from the LA of the patient. Injection tube 524 and delivery shaft 522 can then be removed from the patient while leaving LAA occlusion device 520 covering the ostium of the LAA of the patient. Reference is now made to FIG. 9D, which is another schematic illustration of the LAA occlusion device of FIG. 9C, generally referenced 560, constructed and operative in accordance with a further embodiment of the disclosed technique. FIG. 9D shows the LAA occlusion device without a membrane or a delivery shaft to better illustrate the electrical coupling of the electrical conductors to the conductive fixation splines. Shown in FIG. 9D is an injection tube 562, a positive electrical current conductor 564A, a negative electrical current conductor 564B, an interconnect 566, a positive terminal 568A, a negative terminal 568B and a plurality of conductive fixation splines 570$_1$-570$_6$. These elements are substantially similar to their equivalent elements as shown above in FIG. 9C.

Figure 9D:
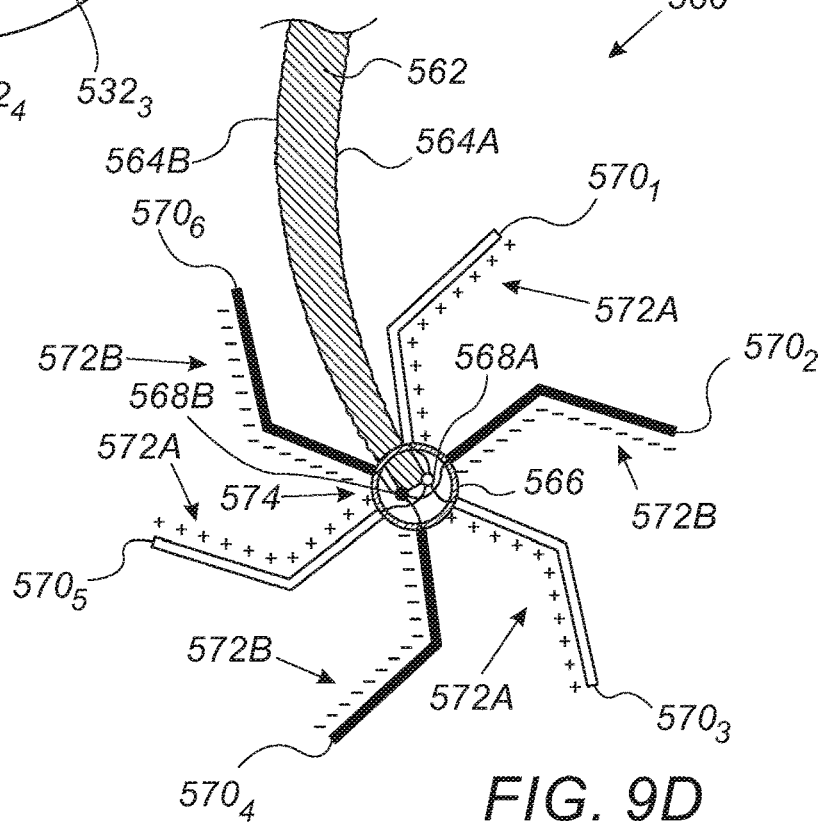
FIG. 9D is another schematic illustration of the LAA occlusion device of FIG. 9C, constructed and operative in accordance with a further embodiment of the disclosed technique.

As can be seen clearer in FIG. 9D, positive electrical current conductor 564A and negative electrical current conductor 564B are coupled to the outer surface of injection tube 562 and substantially form a single element together. Positive electrical current conductor 564A is coupled with positive terminal 568A on interconnect 566 and negative electrical current conductor 564B is coupled with negative terminal 568B on interconnect 566. Positive terminal 568A is electrically coupled with conductive fixation splines 570$_1$, 570$_3$ and 570$_5$, whereas negative terminal 568B is electrically coupled with conductive fixation splines 570$_2$, 570$_4$ and 570$_6$. When an electrical current (either DC or AC or any other kind of phased electricity) is applied to positive electrical current conductor 564A and negative electrical current conductor 564B, positive current is provided via positive terminal 568A to conductive fixation splines $570_1$, $570_3$ and $570_5$, as shown by a plurality of arrows 572A and '+' signs and negative current is provided via negative terminal 568B to conductive fixation splines $570_2$, $570_4$ and $570_6$, as shown by a plurality of arrows 572B and '−' signs. Electric shock vectors (not shown) form between the positively and negatively charged conductive fixation splines thereby electroporating the rim of the ostium of the LAA of the patient (not shown). As can be seen by an arrow 574, the physical and electrical coupling of injection tube 562 along with positive electrical current conductor 564A and negative electrical current conductor 564B has a frangible design such that when injection tube 562 is released or detached from interconnect 566, the electrical connection of positive electrical current conductor 564A and negative electrical current conductor 564B with positive terminal 568A and negative terminal 568B is purposely severed.

It will be appreciated by persons skilled in the art that the disclosed technique is not limited to what has been particularly shown and described hereinabove. Rather the scope of the disclosed technique is defined only by the claims, which follow.

The invention claimed is:

1. A left atrial appendage (LAA) occlusion device comprising:
   a membrane;
   a plurality of fixation splines interweaved into said membrane, for affixing said LAA occlusion device to an ostium of said LAA;
   at least two electrical conductors, also interweaved into said membrane, for applying high voltage electricity to said ostium of said LAA; and
   an interconnect, positioned in said membrane, for electrically coupling said plurality of fixation splines directly with said at least two electrical conductors, wherein said membrane physically occludes said LAA;
   wherein said at least two electrical conductors are used to electroporate said ostium of said LAA via said high voltage electricity, thereby electrically isolating said LAA; and
   wherein said membrane, said plurality of fixation splines, said at least two electrical conductors and said interconnect are permanently left in said ostium of said LAA for endothelialization to occur.

2. The LAA occlusion device according to claim 1, wherein said membrane is selected from a list consisting of:
   a semi-permeable membrane; and
   an impermeable membrane.

3. The LAA occlusion device according to claim 1, wherein said membrane has a shape selected from the group consisting of:
   an umbrella shape;
   a parachute shape;
   a circular shape;
   a balloon shape; and
   a shape which approximates an anatomy of said ostium of said LAA.

4. The LAA occlusion device according to claim 1, further comprising a deployment hub, positioned in said membrane, said deployment hub comprising:
   a threaded aperture; and
   a one-way valve, for enabling a contrast agent entered into said LAA through said deployment hub.

5. The LAA occlusion device according to claim 4, wherein said threaded aperture enables at least one of a catheter and a delivery device to be coupled with said LAA occlusion device for placement in said LAA.

6. The LAA occlusion device according to claim 1, wherein said plurality of fixation splines is made from a biocompatible metal.

7. The LAA occlusion device according to claim 1, wherein said plurality of fixation splines has an open shape and a closed shape.

8. The LAA occlusion device according to claim 1, wherein said plurality of fixation splines is arranged radially around said interconnect.

9. The LAA occlusion device according to claim 1, wherein said plurality of fixation splines is formed in a spring shape and is held under pressure by a delivery sheath.

10. The LAA occlusion device according to claim 1, wherein at least one of a catheter, delivery tube or electrical wire can be coupled with said interconnect for electrically coupling said at least two electrical conductors with a high voltage electricity source.

11. The LAA occlusion device according to claim 1, wherein said at least two electrical conductors are made from a biocompatible conductor material selected from the group consisting of:
    titanium; and
    Nitinol.

12. The LAA occlusion device according to claim 10, wherein said high voltage electricity source is selected from the group consisting of: a direct current electricity source; an alternating current electricity source; and a phased current electricity source.

13. A left atrial appendage (LAA) occlusion device comprising:
    a membrane;
    a plurality of conductive fixation splines, interweaved into said membrane, for affixing said LAA occlusion device to an ostium of said LAA and for conducting electrical current; and
    an interconnect, positioned in said membrane and electrically coupled with said plurality of conductive fixation splines, wherein a positive conductor and a negative conductor can be electrically coupled directly with said interconnect for providing high voltage electricity to said plurality of conductive fixation splines for electroporating said ostium of said LAA;
    wherein said membrane, said plurality of conductive fixation splines and said interconnect are permanently left in said ostium of said LAA for endothelialization to occur.

14. The LAA occlusion device according to claim 13, wherein said membrane is selected from a list consisting of:
    a semi-permeable membrane; and
    an impermeable membrane.

15. The LAA occlusion device according to claim 13, wherein said membrane has a shape selected from the group consisting of:
    an umbrella shape;
    a parachute shape;
    a circular shape;
    a balloon shape; and
    a shape which approximates an anatomy of said ostium of said LAA.

16. The LAA occlusion device according to claim 13, wherein said interconnect is also a deployment hub comprising: a threaded aperture; and a one-way valve, for enabling a contrast agent entered into said LAA through said deployment hub.

17. The LAA occlusion device according to claim 13, wherein said positive conductor and said negative conductor have a frangible design for coupling with said interconnect.

18. The LAA occlusion device according to claim 13, wherein said plurality of conductive fixation splines is made from a biocompatible conductor material selected from the group consisting of:
- titanium; and
- Nitinol.

19. The LAA occlusion device according to claim 13, wherein said plurality of conductive fixation splines has an open shape and a closed shape.

20. The LAA occlusion device according to claim 13, wherein said plurality of conductive fixation splines is arranged radially around said interconnect.

21. The LAA occlusion device according to claim 13, wherein said plurality of conductive fixation splines is formed in a spring shape and is held under pressure by a delivery sheath.

22. The LAA occlusion device according to claim 13, wherein said positive conductor and said negative conductor are coupled with a high voltage electricity source.

23. The LAA occlusion device according to claim 22, wherein said high voltage electricity source is selected from the group consisting of:
- a direct current electricity source;
- an alternating current electricity source; and
- a phased current electricity source.

\* \* \* \* \*